United States Patent

Goldman et al.

Patent Number: 5,120,718
Date of Patent: Jun. 9, 1992

[54] CANDIDA ACID PROTEASE INHIBITING COMPOUNDS

[75] Inventors: Robert C. Goldman, Lake Bluff; William R. Baker, Libertyville; Hwan-Soo Jae, Glencoe; Biswanath De, Vernon Hills; Thomas M. Zydowsky, Waukegan; Edwin de Lara, Vernon Hills, all of Ill.

[73] Assignee: Abbott Laboratories, Abbott Park, Ill.

[21] Appl. No.: 714,820

[22] Filed: Jun. 13, 1991

[51] Int. Cl.⁵ ............... A61K 31/395; A61K 31/415; A61K 31/425; A61K 31/44
[52] U.S. Cl. .................... 514/32; 514/247; 514/252; 514/255; 514/277; 514/408; 514/410; 514/422; 514/426
[58] Field of Search ............... 514/252, 255, 32, 277, 514/408, 410, 422, 426, 247

[56] References Cited

U.S. PATENT DOCUMENTS 4,735,942  4/1988  Heeros et al. ............ 514/252
4,859,670  8/1989  Kamp et al. ............. 514/252
4,870,088  9/1989  Blume et al. ............ 514/255

FOREIGN PATENT DOCUMENTS

WO90/04917  5/1990  PCT Int'l Appl.

OTHER PUBLICATIONS

Ray et al., Infection and Immunity 58 508 (1990).
Tsuobi et al., J. Invest. Dermatol. 85 438 (1985).
Ruchel et al., Zbl. Bakt 273 391 (1990).
Zotter et al., Dermatol. Mon. schr. 176 189 (1990).

Primary Examiner—Nathan M. Nutter
Attorney, Agent, or Firm—Steven R. Crowley

[57] ABSTRACT

Compounds which inhibit Candida acid protease are disclosed which have the formula:

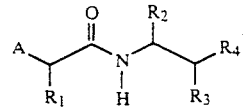

wherein $R_1$ is loweralkyl, loweralkenyl, cycloalkyl, cycloalkenyl, cycloalkylalkyl, cycloalkenylalkyl, arylalkyl or (heterocyclic)alkyl;
$R_2$ is loweralkyl, cycloalkylalkyl or arylalkyl;
$R_3$ is —OH or —NH$_2$;
$R_4$ is
(a) —CH(OH)—$R_5$ wherein $R_5$ is loweralkyl, cycloalkyl or cycloalkylalkyl or
(b) —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl; and
A is

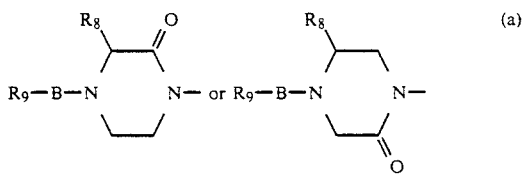

wherein $R_8$ is arylalkyl, B is —C(O) or —S(O)$_2$— and $R_9$ is aryl, arylalkyl, heterocyclic or (heterocyclic)alkyl; or

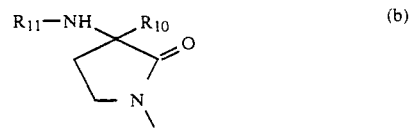

wherein $R_{10}$ is arylalkyl and $R_{11}$ is (a) —C(O)R$_{12}$ wherein $R_{12}$ is alkoxy, arylalkoxy, aryl, arylalkyl, heterocyclic or (heterocyclic)alkyl or (b) —S(O)$_2$—R$_{13}$ wherein $R_{13}$ is aryl, arylalkyl, heterocyclic or (heterocyclic)alkyl; or a pharmaceutically acceptable salt, ester or prodrug thereof.

17 Claims, No Drawings

CANDIDA ACID PROTEASE INHIBITING COMPOUNDS

TECHNICAL FIELD

The present invention relates to compounds and compositions which inhibit Candida acid protease, processes for preparing the compounds and a method of preventing or treating a fungal infection caused by Candida species with a compound of the invention.

BACKGROUND ART

Among the organisms commonly associated with fungal infections in mammals are Candida species. Candida species, in particular *Candida albicans* and *Candida tropicalis*, are commonly found in the oral cavity and intestinal tract of humans. In healthy individuals, Candida species are generally harmless. However, when the immune system of the host is impaired, for example, in neonates, the elderly, burn patients, individuals with AIDS and cancer patients undergoing chemotherapy, Candida species can become pathogenic.

Superficial infections caused by Candida species include oral thrush, denture stomatitis, vulvovaginitis, balanitis, cutaneous candidosis, onychia, paronychia and chronic mucocutaneous candidosis. Systemic infections caused by Candida species include Candida septicemia, renal candidosis, Candida endocarditis, esophageal candidosis, bronchial candidosis and Candida endophthalmitis. Diabetics, denture wearers and AIDS patients are particularly susceptible to Candida species infections.

Agents currently used to treat Candida species infections are amphotericin B, nystatin, flucytosine, ketoconazole, miconazole, clotrimazole, fluconazole and itraconazole and the like. Many of these agents have serious side effects.

It is well-known that Candida species produce an acid protease which is believed to be a virulence factor. Strains of *Candida albicans* which are deficient in or lack this acid protease have reduced virulence when compared to acid protease positive strains. It has been suggested that an inhibitor of the Candida acid protease would be a useful therapeutic agent (Ray, et al., Infection and Immunity 58 508 (1990); Tsuobi, et al., J. Invest. Dermatol. 85 438 (1985); Ruchel, et al., Zbl. Bakt. 273 391 (1990); Zotter, et al., Dermatol. Mon.schr. 176 189 (1990)).

Pepstatin A and chymostatin are known to inhibit Candida acid protease. However, these compounds would not be suitable therapeutics because they are non-specific and are not very potent inhibitors of the enzyme. Therefore, there is a need for agents which are potent and selective inhibitors of Candida acid protease.

DISCLOSURE OF THE INVENTION

In accordance with the present invention there are Candida acid protease inhibiting compounds of the formula:

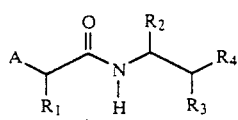
(I)

wherein $R_1$ is loweralkyl, loweralkenyl, cycloalkyl, cycloalkenyl, cycloalkylalkyl, cycloalkenylalkyl, arylalkyl or (heterocyclic)alkyl;

$R_2$ is loweralkyl, cycloalkylalkyl or arylalkyl;

$R_3$ is —OH or —NH$_2$;

$R_4$ is (a) —CH(OH)—$R_5$ wherein $R_5$ is loweralkyl, cycloalkyl or cycloalkylalkyl or (b) —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl; and A is

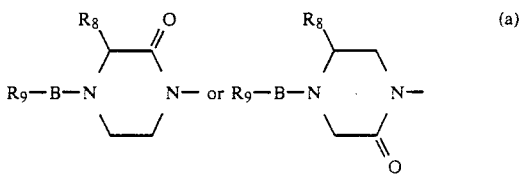
(a)

wherein $R_8$ is arylalkyl, B is —C(O) or —S(O)$_2$— and $R_9$ is aryl, arylalkyl, heterocyclic or (heterocyclic)alkyl; or

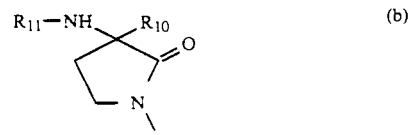
(b)

wherein $R_{10}$ is arylalkyl and $R_{11}$ is (a) —C(O)$R_{12}$ wherein $R_{12}$ is alkoxy, arylalkoxy, aryl, arylalkyl, heterocyclic or (heterocyclic)alkyl or (b) —S(O)$_2$—$R_{13}$ is aryl, arylalkyl, heterocyclic or (heterocyclic)alkyl; or a pharmaceutically acceptable salt, ester or prodrug thereof.

Preferred compounds of the invention are compounds of the formula:

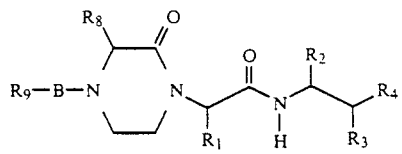

wherein $R_1$ is loweralkyl, loweralkenyl, cycloalkyl, cycloalkenyl, cycloalkylalkyl or cycloalkenylalkyl;

$R_2$ is loweralkyl, cycloalkylalkyl or arylalkyl;

$R_3$ is —OH or —NH$_2$;

$R_4$ is —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl;

$R_8$ is arylalkyl;

B is —C(O) or —S(O)$_2$—; and $R_9$ is aryl, arylalkyl, heterocyclic or (heterocyclic)alkyl; or a pharmaceutically acceptable salt, ester or prodrug thereof.

More preferred compounds of the invention are compounds of the formula:

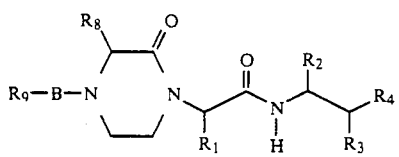

wherein $R_1$ is loweralkyl;

$R_2$ is cycloalkylalkyl;

$R_3$ is —OH;

$R_4$ is —$CH_2CH(R_6)C(O)NHR_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl;

$R_8$ is arylalkyl;

B is —C(O) or —S(O)$_2$—; and $R_9$ is aryl, arylalkyl, heterocyclic or (heterocyclic)alkyl; or a pharmaceutically acceptable salt, ester or prodrug thereof.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkylene" as used herein refers to a straight or branched chain carbon diradical containing from 1 to 7 carbon atoms including, but not limited to, —$CH_2$—, —$CH_2CH_2$—, —$CH(CH_3)CH_2$—, —$CH_2CH_2CH_2$— and the like.

The term "loweralkenyl" as used herein refers to a loweralkyl radical having 2–7 carbon atoms which contains at least one carbon-carbon double bond including, but not limited to, propenyl, butenyl and the like. Alkenyl groups can be unsubstituted or substituted with one or two substituents independently selected from loweralkyl, haloalkyl, cycloalkyl, aryl, heterocyclic, alkoxy, thioalkoxy, amino, alkylamino, dialkylamino, hydroxy, halo, mercapto, nitro, carboxaldehyde, carboxy, alkoxycarbonyl and carboxamide.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one or two substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a loweralkyl radical to which is appended a cycloalkyl group including, but not limited to, cyclohexylmethyl, cyclopentylmethyl and the like.

The term "cycloalkenyl" as used herein refers to a cycloalkyl radical which contains a carbon-carbon double bond including, but not limited to, cyclohexenyl, cyclopentenyl and the like.

The term "cycloalkenylalkyl" as used herein refers to a loweralkyl radical to which is appended a cycloalkenyl group.

The term "aminoalkyl" as used herein refers to a loweralkyl radical to which is appended an —$NH_2$ group.

The term "hydroxyalkyl" as used herein refers to a loweralkyl radical to which is appended an —OH group.

The term "cyanoalkyl" as used herein refers to a loweralkyl radical to which is appended a —CN group.

The term "alkoxyalkyl" as used herein refers to a loweralkyl radical to which is appended an alkoxy group.

The term "thioalkoxyalkyl" as used herein refers to aloweralkyl radical to which is appended a thioalkoxy group.

The term "alkylaminoalkyl" as used herein refers to a loweralkyl radical to which is appended an alkylamino group.

The term "dialkylaminoalkyl" as used herein refers to a loweralkyl radical to which is appended a dialkylamino group.

The term "carboxyalkyl" as used herein refers to a loweralkyl radical to which is appended a carboxy group (—COOH).

The term "alkoxycarbonylalkyl" as used herein refers to a loweralkyl radical to which is appended an alkoxycarbonyl group.

The term "halogen" or "halide" as used herein refers to F, Cl, Br or I.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The terms "alkoxy" and "thioalkoxy" as used herein refer to $R_{20}O$— and $R_{20}S$—, respectively, wherein $R_{20}$ is a loweralkyl group or benzyl.

The term "alkoxyalkoxy" as used herein refers to $R_{21}OR_{22}O$— wherein $R_{21}$ is a loweralkyl group and $R_{22}$ is an alkylene group including, but not limited to, methoxymethoxy, ethoxymethoxy and the like.

The term "polyalkoxy" as used herein refers to —$OR_{23}$ wherein $R_{23}$ is a straight or branched chain containing 2–5, $C_{n'}$—O—$C_{n''}$ linkages wherein n' and n'' are independently selected from 1 to 3 including, but not limited to, methoxyethoxymethoxy and the like.

The term "arylalkoxy" as used herein refers to $R_{24}O$— wherein $R_{24}$ is an arylalkyl group.

The term "alkylamino" as used herein refers to —$NHR_{25}$ wherein $R_{25}$ is loweralkyl.

The term "dialkylamino" as used herein refers to —$NR_{26}R_{27}$ wherein $R_{26}$ and $R_{27}$ are independently selected from loweralkyl.

The term "alkoxycarbonyl" as used herein refers to —$C(O)OR_{28}$ wherein $R_{28}$ is loweralkyl.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "arylalkyl" as used herein refers to a loweralkyl radical to which is appended an aryl group including, but not limited to, benzyl, 4-hydroxybenzyl, 1-naphthylmethyl and the like.

At each occurrence, the term "heterocyclic ring" or "heterocyclic" as used herein independently refers to a 3- or 4-membered ring containing a heteroatom selected from oxygen, nitrogen and sulfur; or a 5- or 6-membered ring containing one, two or three nitrogen atoms; one nitrogen and one sulfur atom; or one nitrogen and one oxygen atom. The 5-membered ring has 0-2 double bonds and the 6-membered ring has 0-3 double bonds. The nitrogen or sulfur heteroatoms can be optionally oxidized. The nitrogen heteroatoms can be optionally quaternized. The term "heterocyclic" also refers to bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Preferred heterocyclics are: azetidinyl, N-methylazetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methylpiperazinyl, pyrimidinyl, pyridazinyl, oxazolyl, oxazolidinyl, isoxazolyl, isoxazolidinyl, morpholinyl, thiomorpholinyl, thiazolyl, 2-aminothiazolyl, thiazolidinyl, isOthiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (=O), alkylimino (R*N= wherein R* a loweralkyl group), amino, alkylamino, dialkylamino, alkoxy, alkoxyalkoxy, polyalkoxy, haloalkyl, cycloalkyl, aryl, arylalkyl, —COOH, —SO₃H and loweralkyl. In addition, nitrogen containing heterocycles can be N-protected.

The term "(heterocyclic)alkyl" as used herein refers to a heterocyclic group appended to a loweralkyl radical, including, but not limited to, imidazolylmethyl, thiazolylmethyl, 3-(morpholin-4-yl)propyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which hereby incorporated by reference. N-protecting groups comprise carbamates, amides, N-alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl, t-butyloxycarbonyl (Boc), benzyloxycarbonyl (Cbz) and the like. N-protecting groups also include an L- or D-aminoacyl residue, which can itself be N-protected.

The term "Ala", as used herein referes to alanine. In general, the amino acid abbreviations follow the IUPAC-IUB Joint Commission on Biochemical Nomenclature for amino acids and peptides (Eur. J. Biochem. 1984, 9-31).

The compounds of the invention (I) can be prepared as shown in Scheme 1. A carboxylic acid 1, or an activated derivative thereof, is coupled to amine 2 using standard peptide coupling methods to provide I. (Carboxylic acid 1 can be prepared according the methods disclosed in PCT Patent Application No. W090/04917, published May 17, 1990 or the Examples provided below.)

Activated derivatives of carboxylic acids as mentioned herein refer to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

SCHEME 1

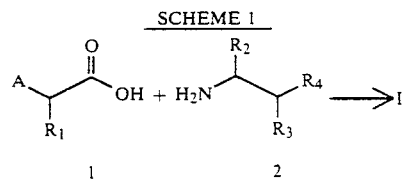

The following Examples will serve to further illustrate preparation of the novel compounds of the present invention.

EXAMPLE 1

(2S)-2-((3R)-3-Benzyl-4-N-(4-methylpiperazin-1-yl-carbonyl)-2-keto-piperazin-1-yl}-hexanoic acid Amide of (2R,4S,5S)-5-amino-6-cyclohexyl-4-hydroxy-2-isopropylhexanoyl N-(n-Butyl)amide Hydrochloride EXAMPLE 1a N-Allyl-D-Phenylalanyl Methyl ester To D-Phenylalanine methyl ester hydrochloride (9.8 g, 45.5 mmol) dissolved in anhydrous dimethylformamide (20 mL), cooled in an ice bath and stirred with a mechanical stirrer was added triethylamine (18.9 mL, 3.0 equiv). Allyl bromide (5.9 mL, 1.5 equiv) was added dropwise under nitrogen with vigorous stirring. The resulting mixture was stirred overnight at room temperature. Ethyl acetate (200 mL) was added and the mixture was washed with saturated sodium bicarbonate solution (2×20 mL), water (50 mL), and brine. The organic phase was dried over sodium sulfate and concentrated under reduced pressure. The residue obtained was chromatographed on silica gel eluting with 1:1 ethyl acetate in hexane to afford the title compound (7.5 g, 75%).

EXAMPLE 1b

N-tert-Butyloxycarbonyl-N-allyl-D-Phenylalanyl Methyl ester

To the compound resulting from Example 1a (7.5 g, 34.25 mmol) dissolved in anhydrous methylene chloride was added di-t-butyl-dicarbonate (9.2 g, 1.2 equiv) in one portion. After stirring overnight at room temperature, the solvent was removed under reduced pressure to afford the title compound in qunatitative yield.

EXAMPLE 1c

N-tert-Butyloxycarbonyl-N-formylmethyl-D-Phenylalanyl Methyl

The compound resulting from Example 1b (4.0 g, 12.53 mmol) was dissolved in methylene chloride (130 mL) and cooled to −78° C. Ozone gas was passed into the solution for 30–40 minutes until the solution turned blue in color. The ozone gas was stopped and replaced by nitrogen gas; dimethyl sulfide (5.0 mL) was addded to the reaction mixture at −78° C. The reaction mixture was stirred overnight at room temperature. The solvent was removed under reduced pressure to afford the title compound.

EXAMPLE 1d

Methyl (2S)-2-((3R)-3-Benzyl-4-N-(4-tert-butylcarbonyl)-2-keto-piperazin-1-yl)-hexanoate To the compound resulting from Example 1c (6.2 g, 19.3 mmol) dissolved in 1:1 methanol and isopropanol (50 mL) and cooled to 0° C. were added added L-Norleucine methyl ester hydrochloride salt (3.5 g, 19.3 mmol) and sodium acetate (4.0 g). After stirring for 40 minutes, sodium cyanoborohydride (1.8 g, 1.5 equiv) was added with stirring. After 2 hours, the solvents were removed under reduced pressure and xylene (100 mL) was added. The mixture was refluxed overnight, cooled to room temperature, and concentrated under reduced pressure. The residue obtained was dissolved in ethyl acetate (200 mL) and washed with saturated ammonium chloride solution (3×60 mL), water, and brine. The organic phase was dried over sodium sulfate and concentrated under reduced pressure to afford the title compound.

EXAMPLE 1e

Methyl (2S)-2-{(3R)-3-Benzyl-4-N-(4-tert-butylcarbonyl)-2-keto-piperazin-1-yl)}-hexanoate The compound resulting from Example 1d was dissolved in 4.0N hydrochloric acid in dioxane, cooled in an ice bath and stirred for 2–3 hours. The mixture was concentrated under reduced pressure, cooled in an ice bath, dissolved in water (20 mL) and neutralized with 2N sodium hydroxide. The product was extracted into ethyl acetate (3×150 mL) and the combined organic extracts washed with water and brine, dried over sodium sulfate and concentrated under reduced presssure. The residue obtained was chromatographed on silica gel eluting with 5% methanol in methylene chloride to afford the title compound (4.3 g, 70% from Example 1c).

EXAMPLE 1f

Methyl 2S-}3R-Benzyl-4-N-(4-methylpiperazin-1-yl-carbonyl)-2-keto-piperazine-1-yl}-hexanoate The compound resulting from Example 1e (4.3 g) was treated with excess phosgene in toluene containing 1.1 equivalents of triethylamine. After stirring at room temperature for 1.5 to 2.0 hours, the reaction mixture was concentrated under reduced pressure. The resulting crude product was dissolved in anhydrous methylene chloride (10 mL) and 1.2 equivalents of N-methylpiperazine was added followed by 1.2 equivalents of triethylamine. After stirring at room temperature for 1 hour, the reaction mixture was concentrated under reduced pressure. Purification by column chromatography on silica gel eluting with ethyl acetate and 5% methanol in methylene chloride afforded the title compound in greater than 90% yield.

EXAMPLE 1g

2S-{3R-Benzyl-4-N-(4-methylpiperazin-1-yl-carbonyl)-2-keto-piperazin-1}-yl-hexanoic acid To the compound resulting from Example 1f (0.64 mmol) dissolved in methanol (10 mL) at room temperature was added 1N lithium hydroxide solution (1.3 mL, 2 equiv). The reaction mixture was stirred overnight at room temperature, cooled to 0° C. and neutralized with 4.0N hydrochloric acid in dioxane (0.33 mL). The solvent was removed under reduced pressure to afford the title compound.

EXAMPLE 1h (2S)-2-{(3R)-3-Benzyl-4-N-(4-methylpiperazin-1-yl-carbonyl) -2-keto-piperazin-1-yl}acid Amide of (2R,4S,5S)-5-amino-6-cyclohexyl-4-hydroxy-2-isopropylhexanoyl N-(n-Butyl)amide Hydrochloride The compound resulting from Example 1g (46.7 mg, 0.109 mmol) and 1-hydroxybenzotriazole (HOBT) (44.2 mg) were dissolved in dimethylformamide (5 mL) under a stream of nitrogen. (2R,4S,5S)-5-Amino-6-cyclohexyl-4-hydroxy-2-isopropylhexanoyl n-butylamide (35.4 mg, 0.109 mmol), prepared as described in PCT Patent Application No. WO90/04917, published May 17, 1990, and N-methylmorpholine (NMM) (15 μL) were added, and the reaction mixture was cooled to −23° C. using a dry ice/carbon tetrachloride bath. After 10 minutes, 1-ethyl-3-(3′-dimethylamino)-propyl-carbodiimide (EDAC) (20.93 mg, 0.109 mmol) was added. The reaction was stirred overnight in the dry ice/carbon tetrachloride bath and then quenched by the addition of saturated sodium bicarbonate (5 mL) and extracted with ethyl acetate (2×100 mL). The combined organic extracts were washed with water and brine, dried over magnesium sulfate, and concentrated under reduced pressure to afford the crude title compound, which was purified by column chromatography on silica gel 60 eluting with 5% methanol in methylene chloride. The residue obtained was dissolved in a minimum amount of methylene chloride, treated with 4.5N HCl in dioxane (2 drops), and triturated with ether to afford the hydrochloride salt (40 mg, 50%). m.p. (free amine) 132°–133° C. The 300 MHz ;$^1$H NMR spectrum was found to be consistent with the proposed structure. Anal calcd for $C_{42}H_{70}N_6O_5 \cdot H_2O$: C, 67.47; H, 9.50; H, 11.24. Found: C, 67.16; H, 9.34; N, 11.13. MS (FAB) m/e 739 $(M+H)^+$. HRMS (FAB) calcd for $C_{42}H_{71}N_6O_5$ m/e 739.5486 $(M+H)^+$. Found m/e 739.5479 $(M+H)^+$.

EXAMPLE 2

(2S)-2-{(3R)-3-Benzyl-4-N-(4-methylpiperazin-1-yl -carbonyl) -2-keto-piperazin-1-yl}-hexanoic acid Amide of (2S,3R,4S)-2-Amino-1-cyclohexyl-3,4-dihydroxyl-6-methylheptane The product of Example 1g (230 mg, 0.535 mmol) was coupled with (2S,3R,4S)-2-amino-1-cyclohexyl-3,4-dihydroxyl-6-methylheptane (130 mg) using the HOBT/NMM/EDAC coupling conditions of Example 1. The reaction was quenched by the addition of saturated sodium bicarbonate (8 mL) and extracted with ethyl acetate (2×100 mL). The combined organic extracts were washed with water and brine, dried over magnesium sulfate, and concentrated under reduced pressure to afford the crude title compound, which was purified by column chromatography on silica gel 60 eluting with 5% methanol in methylene chloride to afford a white solid (155 mg, 45%). m.p. 74°–75° C. The 300 MHz $^1$H NMR spectrum was found to be consistent with the proposed structure. The hydrochloride salt was formed by dissolving the free base in a minimum amount of ether and treating it with a 4.5N HCl in dioxane (2 drops), and triturating with hexane. m.p. 132°–134° C. The 300 MHz $^1$H NMR spectrum was found to be consistent with the proposed structure. Anal calcd for $C_{37}H_{62}ClN_5O_5 \cdot H_2$: C, 62.53; H, 9.01; N, 9.86. Found: C, 62.12; H, 8.80; N, 9.53. MS (DCI/NH$_3$) m/e 656 (M+H)$^+$.

EXAMPLE 3

(2S)-2-{(3R)-3-Benzyl-4-N-(4-methylbenzene-sulfonyl)-6-keto-piperazin-1-yl}-hexanoic acid Amide of (2R,4S,5S)-5-Amino-6-cyclohexyl-4-hydroxy-2-isopropylhexanoyl N-(n-Butyl)amide

EXAMPLE 3a (2S)-2-{3R-benzyl-4-N-(4-methylbenzene-sulfonyl)-6-keto-piperazin-1-yl)-hexanoic acid Methyl (2S)-2-[(3R-benzyl-5-oxo)-piperazin-1-yl]-hexanoate, prepared as described in PCT Patent Application WO 90/04917, published May 17, 1990, (256 mg, 0.80 mmol) was dissolved in methylene chloride (10 mL) and reacted with p-toluenesulfonyl choride (183 mg, 1.2 equiv, 0.96 mmol) and triethylamine (0.17 mL, 1.5 equiv) at room temperature. The resulting mixture was stirred for 2 hours and then ethyl acetate (100 mL) was added. The mixture was washed with water (2×5 mL) and brine, dried over sodium sulfate and concentrated under reduced pressure. The residue obtained was chromatographed on silica gel eluting with 25% ethyl acetate in hexane to afford methyl (2S)-2-{3R-benzyl-4-N-(4-methylbenzene-sulfonyl)-6-keto-piperazin-1-yl)-hexanoate (300 mg, 80%). This compound was hydrolyzed by the procedure described in Example 1g to afford the title compound.

EXAMPLE 3b (2S)-2-{(3R)-3-Benzyl-4-N-(4-methylbenzene-sulfonyl)-6-keto-piperazin-1-yl}-hexanoic acid Amide of (2R,4S,5S)-5-Amino-6-cyclohexyl-4-hydroxy-2-isopropylhexanoyl N-(n-Butyl)amide (2S)-2-(3R-Benzyl-4-N-(4-methylbenzene-sulfonyl)-6-keto-piperazin-1-yl}-hexanoic acid (100 mg, 0.218 mmol) was coupled with (2R,4S,5S)-5-amino-6-cyclohexyl-4-hydroxy-2-isopropylhexanoyl N-(n-butyl)amide (71 mg, 1 equiv) using the HOBT/NMM/EDAC coupling conditions. The reaction was quenched by the addition of saturated sodium bicarbonate (10 mL) and extracted with ethyl acetate (2×100 mL). The combined organic extracts were washed with water and brine, dried over magnesium sulfate, and concentrated under reduced pressure to afford the crude title compound, which was purified by column chromatography on silica gel 60 eluting with 1:1 ethyl acetate/hexane to afford a white solid (77 mg, 50%). The 300 MHz $^1$H NMR spectrum was found to be consistent with the proposed structure. MS (DCI/NH$_3$) m/e 767 (M+H)$^+$.

EXAMPLE 4

(2S)-2-(3-Benzyl-4-N-(p-methylbenzyl-sulfonyl)-2-keto-piperazin-1-yl)-hexanoic acid Amide of (2R,4S,5S)-5-Amino-6-cyclohexyl-4-hydroxy-2-isopropylhexanoyl N-(n-Butyl)amide Using the procedure described in Example 3a, the compound resulting from Example 1e was reacted with benzyl-sulfonyl chloride, and the resulting methyl ester was hydrolyzed using the procedure described in Example 1g to give (2S)-2-{3-Benzyl-4-N-(p-methylbenzyl-sulfonyl)-2-keto-piperazin-1-yl}-hexanoic acid. To a solution of this compound (230 mg, 0.48 mmol), HOBT (202 mg, 1.5 mmol), (2R,4S,5S)-5-amino-6-cyclohexyl-4-hydroxy-2-isopropylhexanoyl N-(n-butyl)amide (158 mg, 0.48 mmol) and triethylamine (139 μL, 1 mmol) in dimethylformamide (5 mL) at 0° C. was added EDAC (96 mg, 0.5 mmol). The reaction mixture was stirred at room temperature overnight and then diluted with ethyl acetate and aqueous sodium bicarbonate solution. Normal work up and chromatographic purification afforded the title compound (237 mg, 64%) as a mixture of diastereomers. The 300 MHz $^1$H NMR spectrum was found to be consistent with the proposed structure. MS (DCI/NH3) m/e 767 (M+H)$^+$.

EXAMPLE 5

(2S)-2-{(3R)-3-Benzyl-4-N-(4-methoxybenzene-sulfonyl)-2-keto-piperazin-1-yl}-hexanoic acid Amide of (2R,4S,5S)-5-Amino-6-cyclohexyl-4-hydroxy-2-isopropylhexanoyl N-(n-Butyl)amide Using the procedure described in Example 3a, the compound resulting from Example 1e was reacted with 4-methoxybenzenesulfonyl chloride, and the resulting methyl ester was hydrolyzed using the procedure described in Example 1 g. The step involving hydrochloric acid in dioxane was omitted to afford the lithium salt of (2S)-2-{(3R)-3-benzyl-4-N-(4-methoxybenzene-sulfonyl)-2-keto-piperazin-1-yl}-hexanoic acid. This salt (50 mg, 0.11 mmol) was coupled with (2R,4S,5S)-5-amino-6-cyclohexyl-4-hydroxy-2-isopropylhexanoyl N-(n-butyl)amide (35.9 mg, 0.11 mmol) using the HOBT/NMM/EDAC coupling procedure. The reaction was quenched with saturated sodium bicarbonate solution and extracted with ethyl acetate (2×100 mL). The combined organic extracts were washed with water and brine, dried over sodium sulfate, and concentrated In vacuo to afford crude title product. Purification by column chromatography on silica gel 60 eluting with 15% ethyl acetate in hexane afforded the title product (52 mg, 60%). The 300 MHz $^1$H NMR spectrum was found to be consistent with the proposed structure. Anal calcd for $C_{43}H_{66}N_4O_7S \cdot 1.5\ H_2O$: C, 63.78; H. 8.53; N, 6.92. Found: C, 63.60; H, 8.09; N, 6.92. MS (DCI/NH3) m/e 783 (M+H)$^+$.

EXAMPLE 6

(2S)-2-{(3S)-3-Benzyl-4-N-(4-methylbenzene-sulfonyl)-6-keto-piperazin-1-yl}-hexanoic acid Amide of (2R,4S,5S)-5-Amino-6-cyclohexyl-4-hydroxy-2-isopropylhexanoyl N-(n-Butyl)amide

EXAMPLE 6a

N-tert-Boc-N-Benzyloxvcarbonylmethyl-Phenylalanino)

L-Phenylalaninol (10.0 g, 66.13 mmol) was reacted with benzyl 2-bromoacetate following a published procedure (J. Org. Chem., 110, 1547, 1988) to afford the alkylated product. MS (DCI/NH$_3$) m/e 300 (M+H)$^+$. This product was dissolved in methylene chloride (100 mL), cooled to 0° C., and treated with di-t-butyl-dicarbonate (15.27 g, 70 mmol). After stirring at room temperature overnight, the solvent was removed under reduced pressure to afford the title compound.

EXAMPLE 6b

N-tert-Boc-N-Benzyloxycarbonylmethyl-Phenylalanal

To a solution of the product of Example 6a (10.0 g, 25 mmol) and triethylamine (10 mL, 75 mmol) in methylene chloride (50 mL) at 0° C. was added sulfur trioxide pyridine complex (12.0 g) in dimethyl sulfoxide (25 mL). The reaction mixture was allowed to gradually warm to room temperature over two hours and then diluted with ether and aqueous sodium bicarbonate solution. The ether layer was washed with brine, dried over magnesium sulfate, and concentrated In vacuo to give the title compound (9.45 g). MS (DCI/NH$_3$) m/e 398 (M+H)$^+$.

EXAMPLE 6c (2R)-2-(N-tert-Boc-N-Benzyloxycarbonylmethyl-)Amino-3-Phenylpropyl Amide of Norleucine Methyl ester To the product of Example 6b (4.5 g, 113 mmol) and the methyl ester of L-Norleucine (I.61 g, 11.26 mmol) in isopropanol (25 mL) was added sodium cyanoborohydride (1.51 g, 24 mmol). The reaction mixture was stirred overnight at room temperature and quenched with aqueous hydrochloric acid. The reaction mixture was basified with aqueous sodium hydroxide solution and then extracted with ethyl acetate. The combined organic extracts were washed with brine, dried over magnesium sulfate, and concentrated in vacuo to afford a residue which was column chromatographed to give the title compound (3.25 g, 53%). MS (DCI/NH3) m/e 527 (M+H)$^+$.

EXAMPLE 6d (2S)-2-{(3S)-3-Benzyl-4-N-Boc-6-keto-piperazin-1-yl}-hexanoic acid Amide of Norleucine Methyl ester The producat of Example 6c (410 mg, 0.75 mmol) was dissolved in methanol (10 mL) and treated with 10% palladium on charcoal (100 mg) under a hydrogen atmosphere at room temperature for two hours. The catalyst was removed by filtration and the solution concentrated under reduced pressure to afford the carboxylic acid.

The carboxylic acid from above was dissolved in dimethylformamide (5 mL) and treated with 1-ethyl-3-(3'-dimethylamino)-propylcarbodiimide (EDAC) (80 mg, 0.41 mmol) in the presence of 1-hydroxybenzotriazole hydrate (HOBT) (162 mg, 0.84 mmol) and triethylamine (70 μL) at room temperature overnight. Work up and purification by column chromatography afforded the title compound (162 mg, 51%). MS (DCI/NH3) m/e 419 (M+H)$^+$.

EXAMPLE 6e (2S)-2-{(3S)-3-Benzyl-4-N-(4-methylbenzene-sulfonyl)-6-keto-piperazin-1-yl}-hexanoic acid Amide of Norleucine Methyl ester The product of Example 6d (1.85 g, 4.42 mmol) was dissolved in 4.5N hydrochloric acid in dioxane and stirred at room temperature for two hours. The reaction mixture was concentrated under reduced pressure to afford the amine hydrochloride salt.

To the salt dissolved in pyridine (10 mL) at 0° C. was added p-toluenesulfonyl chloride (1.69 g, 8.86 mmol). The reaction mixture was allowed to warm gradually to room temperature over 6 hours and then was diluted with ethyl acetate and water. The excess pyridine was removed by washing with aqueous hydrochloric acid. The combined organic extracts were washed with brine, dried over magnesium sulfate, and concentrated at reduced pressure to give the title compound (1.63 g, 78%). MS (DCI/NH$_3$) m/e 473 (M+H)$^+$, 490 (M+H+NH$_3$)$^+$. The 300 MHz $^1$H NMR spectrum was found to be consistent with the proposed structure.

EXAMPLE 6f (2S)-2-{(3S)-Benzyl-4-N-(4-methylbenzene-sulfonyl)-6-keto-piperazin-1-yl-hexanoic acid Amide of (2R,4S,5S)-5-Amino-6-cyclohexyl-4-hydroxy-2-isopropylhexanoyl N-(n-Butyl)amide To the product of Example 6e (820 mg, 1.73 mmol) dissolved in methanol (10 mL) was added a solution of sodium hydroxide (510 mg, 12.75 mmol) in water (3 mL). The reaction mixture was stirred at room temperature for 90 minutes, then cooled to 0° C. and acidified with aqueous sodium hydrogen sulfate and extracted with ethyl acetate. The combined organic extracts were washed with brine, dried over magnesium sulfate, and concentrated in vacuo to afford the carboxylic acid (678 mg, 85%).

To a solution of the carboxylic acid (140 mg, 0.33 mmol), HOBT (162 mg, 1.20 mmol), (2R,4S,5S)-5-amino-6-cyclohexyl-4-hydroxy-2-isopropylhexanoyl N-(n-butyl)amide (97 mg, 0.29 mmol) and triethylamine (55 μL, 0.39 mmol) in dimethylformamide (3 mL) at 0° C. was added EDAC (62 mg, 0.32 mmol). The reaction mixture was stirred at room temperature overnight and then poured into a mixture of aqueous sodium bicarbonate and ether. Work up and purification including column chromatography afforded the title compound (132 mg, 52%). $^1$H NMR (CDCl$_3$, 300 MHz) δ 0.80–2.00 (m, 37H), 2.40 (s, 3H), 2.77 (m, 2H), 3.15–3.60 (m, 6H), 3.68 (d, J=18 Hz, 1H), 3.88 (m, 1H), 4.22 (m, 1H), 4.33 (d, J=18Hz, 1H), 4.68 (t, J=7 Hz, 1H), 5.97 (t, J=6 Hz, 1H), 6.49 (d, J=9 Hz, 1H), 7.20 (d, J=8Hz, 2H), 7.28 (m, 7H), and 7.60 (d, J =8Hz, 2H). MS (DCI/NH$_3$) m/e 749 (M+H)$^+$, 767 (M+H+NH$_3$)$^+$.

EXAMPLE 7

(2S)-2-{(3S)-3-Benzyloxycarbonylamino-3-benzyl-2-keto-pyrrolidin-1-yl}-4-methylthio-butanoic acid Amide of (2S,3R,4S)-2-Amino-1-cyclohexyl-3,4-dihydroxyl-6-methylheptane

EXAMPLE 7a (2S,5S)-N-Benzyloxycarbonyl-2-phenyl-5-benzyl-1,3-oxazolin-4-one

N-Benzyloxycarbonyl-Phenylalanine (25.0 g, 83.53 mmol), p-toluenesulfonic acid monohydrate (16.05 g, 83.53 mmol), and benzaldehyde (17.15 mL, 167 mmol) were combined in 1,1,1-trichloroethane (300 mL) and warmed to reflux under a heavier than water solvent separating adapter. After 21 hours at reflux, the reaction was cooled to room temperature, treated with 1M sodium metabisulfite (100 mL), and stirred overnight. The by-product was removed by filtration and washed with chloroform. The filtrate was washed with IM hydrochloric acid (100 mL), saturated sodium bicarbonate (100 mL), water (100 mL), and brine (100 mL), dried over magnesium sulfate, and concentrated under reduced pressure to afford crude product as an oil. Flash chromatography on silica gel eluting with 20% ethyl acetate in hexane followed by a second column eluting with 10% ethyl acetate in hexane afforded the product as a solid which was recrystallized from ethyl acetate/- hexane to afford pure title compound. m.p. 121°–122° C. The 300 MHz $^1$H NMR spectrum was found to be consistent with the proposed structure. MS (DCI/NH$_3$) m/e 388 (M+H)$^+$.

EXAMPLE 7b (2S,5S)-N-Benzyloxycarbonl-2phenyl-5-benzyl-5-allyl-1.3-oxazolin-4-one To the product of Example 7a (4.30 g, 11.1 mmol) dissolved in tetrahydrofuran (30 mL) and cooled to −78° C. in a dry ice/acetone bath was added 1.0 M sodium bis(trimethylsilyl)amide in tetrahydrofuran (12.21 mL, 12.21 mmol) dropwise. After stirring at −78° C. for 30 minutes, allyl bromide (1.46 mL, 16.65 mmol) was added dropwise. The reaction mixture was stirred at −78° C. and allowed to gradually warm to room temperature over 2 hours. The reaction was quenched by the addition saturated ammonium chloride solution (50 mL) and stirred for 30 minutes. The reaction mixture was extracted with ethyl acetate (200 mL, 2 ×20 mL); the combined organic extracts were washed with brine (20 mL), dried over magnesium sulfate, and concentrated under reduced pressure to afford crude material. Flash chromatography on silica gel eluting with 10% ethyl acetate in hexane afforded the title compound as a solid. m.p. 65°–66° C. The 300 MHz $^1$H NMR spectrum was found to be consistent with the proposed structure. MS (DCI/NH$_3$) m/e 428 (M+H)$^+$.

EXAMPLE 7c (2S,5S)-N-Benzyloxycarbonyl-2-phenyl-5-benzyl-1,3-oxazolin-4-one-5-yl}acetaldehyde The product of Example 7b (300 mg, 0.702 mmol) was dissolved in methylene chloride (35 mL), cooled to −78° C., and treated with ozone gas until a cloudy blue color persisted. The ozonator was shut off and oxygen was bubbled through the reaction mixture until the color dissipated while maintaining the temperature at −78° C. The reaction was quenched with dimethylsulfide and allowed to warm to room temperature, stirred for 5 minutes, and then concentrated at reduced pressure. The residue was chased with two portions of methylene chloride to afford the title compound (344 mg, 100%).

EXAMPLE 7d

Boc-Methionine Amide of (2S,3R,4S)-2-Amino-1-cyclohexyl-3,4-dihydroxyl-6-methylheptane Boc-Methionine (1.28 g, 5.14 mmol) was coupled with (2S,3R,4S)-2-amino-1-cyclohexyl-3,4-dihydroxyl-6-methylheptane (1.25 g, 5.14 mmol) using N-methylmorpholine (NMM) (0.571 mL, 5.14 mmol) and isobutylchloroformate (IBCF) (0.673 mL, 5.14 mmol) as the coupling reagents. The coupled product was used without further purification.

The coupled product from above (2.5 g, 5.27 mmol) was dissolved in 4.5M hydrochloric acid in dioxane and allowed to stand for 1 hour. Chloroform was added and the aqueous phase made basic with aqueous sodium carbonate. The aqueous phase was extracted with two additional portions of chloroform. The combined organic extracted were dried over sodium sulfate and concentrated under reduced pressure to afford the crude product as a solid. Flash chromatography on silica gel eluting with 2.5% methanol in chloroform afforded the title compound. The 300 MHz $^1$H NMR spectrum was found to be consistent with the proposed structure.

EXAMPLE 7e (2S)-2-{(3S)-3-Benzyloxycarbonylamino-3-benzyl-2-keto-pyrrolidin-1-yl}-methylthio-butanoic acid Amide of (2S,3R, 4S)-2-Amino-1-cyclohexyl-3,4-dhydroxyl-6-methylheptane The product of Example 7c (121 mg, 0.2468 mmol) was reacted with the product of Example 7d (100.3 mg, 0.2468 mmol) by the procedure described in Example 8 except that the reaction was allowed to proceed for 3 days. Work up and purification by flash chromatography on silica gel eluting with 10% ether in chloroform afforded the title compound (88 mg, 53%). The 300 MHz $^1$H NMR spectrum was found to be consistent with the proposed structure. m.p. 61°–63° C.

EXAMPLE 8

(2S)-2-{(3S)-3-Benzyloxycarbonylamino-3-benzyl-2-keto-pyrrolidin-1-yl)-hexananoic acid Amide of (2S,3R,4S)-2-Amino-1-cyclohexyl-3,4-dihydroxyl-6-methylheptane The producat of Example 7c (118.3 mg, 0.2411 mmol), H-Nle-{(2S,3R,4S)-2-Amino-1-cyclohexyl-3,4-dihydroxyl-6-methylheptane} (96.7 mg, 0.2411 mmol), prepared in analogy to Example 7d from the dicyclohexylamine salt of Boc-Norleucine, and sodium acetate (20.6 mg, 0.2411 mmol) were taken up in methanol (2 mL). Molecular sieves were added followed by glacial acetic acid (13.8 µL, 0.2411 mmol). Sodium cyanoborohydride (15.9 mg, 0.2411 mmol) was added, and the reaction mixture was allowed to stir for 26 hours. The reaction was quenched by the addition of 1N hydrochloric acid (0.5 mL) and then basified by the addition of 3M sodium carbonate solution (0.5 mL) and extracted with ethyl acetate (2×50 mL). The combined organic extracts were washed with brine, dried over sodium sulfate, and concentrated under reduced pressure. The residue obtained was flash chromatographed on silica gel eluting with 10–15% ether in chloroform to afford the title product as a white amorphous solid. m.p.61°–63° C. The 300 MHz $^1$H NMR spectrum was found to be consistent with the proposed structure.

EXAMPLE 9

(2S)-3-(4-Thiazolyl)-2-{(3R)-3-benzyl-4-N-(4-methylbenzenesulfonyl) -2-keto-piperazin-1-y}-propionic acid Amide of (2R,4S,5S)-5-Amino-6-cyclohexyl-4-hydroxy-2-isopropylhexanoyl N-(n-Butyl)amide The title compound was prepared as described in PCT Patent Application WO90/04917, published May 17, 1990.

EXAMPLE 10

(2S)-2-{(3S)-3-Benzyl-4-N-(4-methylpiperazinyl-carbonyl)-2-keto-piperazinyl-1-yl-hexanoic acid Amide of (2S,3R,4S)-2-Amino-1-cyclohexyl-3,4-dihydroxyl-6-methylheptane Hydrochloride (2S)-2-{(3S)-Benzyl-4-N-(4-methylpiperazin-1-yl-carbonyl)-2-keto-piperazinyl-1-yl}-hexanoic acid was prepared in analogy to Examples 1a–g starting with L-Phenylalanine methyl ester hydrochloride instead of D-Phenylalanine methyl ester hydrochloride. This carboxylic acid (200 mg, 0.47 mmol) was coupled with (2S,3R,4S)-2-amino-1-cyclohexyl-3,4-dihydroxyl-6-methylheptane (132 mg) by the HOBT/NMM/EDAC procedure to afford crude product. Purification by flash chromatography on silica gel eluting with ethyl acetate followed by 5% methanol in methylene chloride afforded the title compound and its 3R-benzyl diastereomer as their free bases. Each free base was dissolved in ether (2 mL) and treated with 4.5N hydrochloric acid in dioxane to afford the diastereomeric hydrochloride salts. The title compound was obtained in 30% (50 mg). The 300 MHz $^1$H NMR spectrum was found to be consistent with the proposed structure. MS (DCI/NH3) m/e 656 (M+H)+.

EXAMPLE 11

(2S)-2-{(3R)-3-Benzyl-4-N-(4-(methylamino)benzene-sulfonyl)-2-keto-piperazin-1-yl}-hexanoic acid Amide of (2S,3R,4S)-2-Amino-1-cyclohexyl-3,4-dihydroxyl-6-methylheptane Using the procedure described in Example 3a, the compound resulting from Example 1e was reacted with 4-(methylamino)benzenesulfonyl chloride to give methyl (2S)-2-{(3R)-3-benzyl-4-N-(4-(methylamino)-benzene-sulfonyl)-2-keto-piperazin-1-yl}-hexanoate. Hydrolysis by the procedure described in Example 1g but omitting the acid neutralization salt was coupled with (2S,3R,4S)-2-amino-1-cyclohexyl-3,4-dihydroxyl-6-methylheptane (500 mg, 1 equiv) using the HOBT/NMM/EDAC procedure to afford crude material. Purification by flash chromatography eluting with 25–33% ethyl acetate in hexane afforded the title compound (325 mg, 47%). The 300 MHz $^1$H NMR spectrum was found to be consistent with the proposed structure. Anal calcd for $C_{38}H_{58}N_4O_6S \cdot 0.5H_2O$: C, 64.41; H, 8.83; N, 7.91. Found: C, 64.49; H, 7.98; N, 7.70. MS (FAB) m/e 699 (M+H)+.

EXAMPLE 12

(2S)-2-{(3S)-3-Benzyl-4-N-(4-methylpiperazin-1-yl-carbonyl)-2-keto-piperazin-1-yl}-hexanoic acid Amide of (2R,4S,5S)-5-Amino-6-cyclohexyl-4-hydroxy-2-isopropylhexanoyl N-3-(N-Morpholinyl)propyllamide (2S)-2-{(3S)-3-Benzyl-4-N-(4-methylpiperazin-1-yl-carbonyl)-2-keto-piperazin-1-yl }-hexanoic acid (413 mg, 0.96 mmol) was coupled with (2R, 4S,5S)-5amino-6-cyclohexyl-4-hydroxy-2-isopropylhexanoyl N-[3-(N-morpholinyl)propyl]amide (PCT Patent Application No. W090/03971, published Apr. 19, 1990) (639 mg, 1 equiv) using the HOBT/NMM/EDAC procedure. The crude product was purified by flash chromatography on silica gel eluting with 0.17% triethylamine/6.7% methanol/93.17% methylene chloride to afford the title compound (170 mg, 22%). The 300 MHz $^1$H NMR spectrum was found to be consistent with the proposed structure. Anal calcd for $C_{45}H_{75}N_7O_6 \cdot 3H_2O$: C, 62.57; H, 9.38; N, 11.36. Found: C, 62.48; H, 8.94; N, 11.52. MS (FAB) m/e 810 (M+H)+. HRMS (FAB) calcd for $C_{45}H_{76}N_7O_6$ m/e 810.5857 (M+H)+. Found m/e 810.5859 (M+H)+.

EXAMPLE 13

(2S)-2-{(3S)-3-Benzyl-4-N-(4-methylpiperazin-1-yl-sulfonyl)-2-kero-piperazin-1-yl) -}hexanoic acid Amide of (2R,4S, 5S,)-5-amino-6-cyclohexyl-4-hydroxy-2-isopropylhexanoyl N-(n-Butyl)amide

EXAMPLE 13a (2S)-2-{(3S)-3-Benzyl-4-N-(4-methylpiperazin-1-yl-sulfonyl)-2-keto-piperazin}-1-yl1-hexanoic acid Methyl ester To the compound resulting from Example 1e (400 mg, 1.26 mmol) dissolved in anhydrous methylene chloride (10 mL) was added triethylamine (4 equiv) and 4-methylpiperazin-1-yl-sulfonyl chloride hydrochloride (440 mg, 1.89 mmol) followed by dimethylaminopyridine (DMAP) (10 mg). The reaction mixture was stirred overnight at room temperature and then quenched by the addition of water (10 mL) and ethyl acetate (100 mL). The organic phase was washed with brine, dried over sodium sulfate, and concentrated under reduced pressure to afford crude product. Purification by flash chromatography eluting with ethyl acetate followed by 5% methanol in methylene chloride afforded the title product (500 mg, 83%). The 300 MHz $^1$H NMR spectrum was found to be consistent with the proposed structure. MS (DCI/NH3) m/e 481 (M+H)+.

EXAMPLe 13b (2S)-2-{(3S)-3-Benzyl-4-N-(4-methylpiperazin-1-yl-sulfonyl)-2-keto-piperazin-1-yl}-hexanoic acid Amide of (2R,4S,5S)-5-amino-6-cyclohexyl-1-hydroxy-2-isopropylhexanoyl N-(n-Butyl)amide The prOduct of Example 13a (180 mg, 0.375 mmol) was hydrolyzed with lithium hydroxide in methanol to afford the carboxylic acid. The carboxylic acid was coupled with (2R,4S,5S)-5-amino-6-cyclohexyl-4-hydroxy-2-isopropylhexanoyl N-(n-butyl)amide (123 mg,) by the HOBT/NMM/EDAC procedure to afford crude material. Purification by column chromatography on silica gel eluting with ethyl acetate followed by 5% methanol in methylene choride afforded the title compound (145 mg, 50%). m.p. 104°–105° C. The 300 MHz $^1$H NMR spectrum was found to be consistent with the proposed structure. Anal calcd for $C_{41}H_{70}N_6O_6S$: C, 63.56; H, 9.04; N, 10.85. Found: C, 63.11; H, 8.79; N, 10.38. MS (FAB) m/e 775 (M+H)+.

EXAMPLE 14

2S-(3S-Benzyl-4-N-(4-methoxymethoxypiperidinyl-carbonyl)-2-keto-piperazin-1-yl)-hexanoic acid Amide of (2R,4,5S) -5-Amino-6-cyclohexyl-4-hydroxy-2-isopropylhexanoyl N-(n-Butyl)amide

EXAMPLE 14a (2S)-2-}(3S)-3-Benzyl-4-N-(4-methoxymethoxypiperidin-1-yl-carbonyl) -2-keto-piperazin-1-yl)-hexanoic acid Methyl ester To (2S)-2-{(3S)-3-Benzyl-4-N-(chloroformyl)-2-keto-piperazin-1-yl}-hexanoic acid methyl ester dissolved in methylene chloride at 0° C. was added 4-methoxymethoxypiperidine (1.2 equiv) and triethylamine (2 equiv). The reaction mixture was allowed to gradually warm to room temperature over 2 hours. Water was added and the mixture was extracted with ethyl acetate. The combined organic extracts were washed with brine, dried over sodium sulfate, and concentrated under reduced pressure. The crude product was flash chromatographed eluting with 1:1 ethyl acetate/hexane to afford the title compound as a colorless oil (800 mg, 98%). The 300 MHz $^1$H NMR spectrum was found to be consistent with the proposed structure. HRMS (DCI/NH3) calcd for $C_{26}H_{40}N_3O_6$ m/e 490.2917 (M+H)+. Found m/e 490.2916 (M+H)+.

EXAMPLE 14b (2S)-2{(3)-3-Benzyl-4-N-(4-methoxymethoxypiperidin-1yl-carbonyl)-2-keto-piperazin -1yl}-hexanoic acid Amide of (2R,4S,5S)-5-Amino-6-cyclohexyl-4-hydroxy-2-isopropylhexanoyl N-(n-Butyl)amide The product of Example 14a (200 mg, 0.41 mmol) was converted to its lithium salt using lithium hydroxide in methanol. This salt was coupled with (2R,4S,5S)-5-amino-6-cyclohexyl-4-hydroxy-2-isopropylhexanoyl N-(n-butyl)amide, using the HOBT/NMM/EDAC procedure to afford crude material. Purification by flash chromatography eluting with 1:1 ethyl acetate/hexane followed by ethyl acetate afforded the tital product (180 mg, 56%). m.p. 149°–150° C. The 300 MHz $^1$H NMR spectrum was found to be consistent with the proposed structure. Anal calcd for $C_{44}H_{73}N_5O_7$: C, 67.44; H, 9.32; N, 8.94. Found: C, 67.38; H, 9.63; N, 8.83.

EXAMPLE 15

(2S)-2-{(3S)-3-Benzyl-4-N-(4-methylpiperazin-1-yl-sulfonyl)-2-keto-piperazine-1-yl }-hexanoic acid Amide of (2R,4S,5S)-5-Amino-6-cyclohexyl-4hydroxy-2-isopropylhexanoyl N-[3-(N-Morpholinyl)propyl]amide (2S)-2-{(3S)-3-Benzyl-4N-(4-methylpiperazine-1-yl-sulfonyl)-2-keto-piperazine-1-yl }-hexanoic acid Amide of (2R,4S,5S)-5-Amino-6-cyclohexyl-4hydroxy-2-isopropylhexanoyl N-[3-(N-Morpholinyl)propyl]amide (2S)-2-{(3S)-3-Benzyl-4-N-(4-methylpiperazine-1-yl-sulfonyl) -2-keto-piperazin-1-yl}-hexanoic acid (200 mg, 0.43 mmol), prepared as described in Example 13 and hydrolyzed with lithium hydroxide in methanol, was coupled with (2,4S,5S)-5-amino-6-cyclohexyl-4-hydroxy-2-isopropylhexanoyl N-[3-(N-morpholinyl)-propyl]amide (170 mg, 0.43 mmol) by the HOBT/NMM/EDAC procedure to afford crude product. Purification by flash chromatography eluting with 5–7% methanol in methylene chloride afford the title compound (107 mg, 29%). The 300 MHz $^1$H NMR spectrum was found to be consistent with the proposed structure. Anal calcd for $C_{44}H_{75}N_7O_7S$: C, 62.45; H, 8.93; N, 11,58. Found: C, 63.37; H, 8.96; N, 11.61. MS (FAB) m/e 846 (M+H)$^+$.

EXAMPLE 16

(2S)-2-{(3S)-3-Benzyl-4-N-(4-methoxymethoxypiperidin-1-yl-carbonyl)-2-keto-piperazin -1-yl}-hexanoic acid Amide of (2R, 4S, 5S)-5-Amino-6-cyclohexyl-4-hydroxy-2-isopropylhexanoyl N-[3-(N-Morpholinyl)propyl]amide (2S)-2-{(3S)-3-Benzyl-4-N-(4methoxymethoxypiperidin-1-yl-carbonyl)-2-keto-piperazin -1-yl}-hexanoic acid (200 mg, 0.42 mmol) was coupled with (2R,4S,5S)-5-amino-6-cyclohexyl-4-hydroxy-2-isopropylhexanoyl N-[3-(N-morpholinyl)propyl]amide (167 mg, 0.42 mmol) by the Purification by flash chromatography on siilca gel eluting with 5–6% methanol in methylene chloride afforded the title product (160 mg, 45%). The 300 MHz $^1$H NMR spectrum was found to be consistent with the proposed structure. Anal calcd for $C_{47}H_{78}N_6O_8$: C, 66.01; H, 9.19; N, 9.83. Found: C, 65.68; H, 98.81; N, 9.75. MS (FAB) m/e 855 (M+H)$^+$.

EXAMPLE 17

(2)-2-{(3R)-3-Benzyl-4-N-(4-methylpiperazin-1-yl-carbonyl)-2-keto-piperazin-1-yl}-hexanoic acid Amide of (2S,4S,5S)-5-Amino-6-cyclohexyl-4-hydroxy-2-isopropylhexanoyl N-[2-Dimethylamino)ethyl]amide (2S)-2-{(3)-3-Benzyl-4-N-(4-methylpiperazin-1-yl-carbonyl)-2-keto-piperazin-1-yl}-hexanoic acid (200 mg, 0.465 mmol was coupled with (2R,4S,5S)-5-amino-6-cyclohexyl-4-hydroxy-2-isopropylhexanoyl N-[2-(dimethylamino)ethyl]amide (158 mg), prepared in analogy with the methods outlined in PCT Patent Application WO 90/04917, published May 17, 1990, by the HOBT/NMM/EDAC procedure to afford crude product. Purification by flash chromatography on silic gel eluting with 7–8% methanol and 1% ammonium hydroxide in methylene chloride afforded the title product (170 mg, 48%). The 300 MHz $^1$H NMR spectrum was found to be consistent with the proposed structure. m.p. 114°–115° C. Anal calcd for $C_{42}H_{71}n_7O_5 \cdot 0.5H_2O$: C, 66.06; H, 9.44; N, 12.84. Found: C, 66.22; H, 9.60; N, 12.91. MS (FAB) m/e 754 (M+H)$^+$.

EXAMPLE 18

(2S)-2-{(3R)-3-Benzyl-4-N-(4-methylpiperazin-1-yl-carbonyl)-2-keto-piperazin-1-yl}-hexanoic acid Amide of (2R,4S,5S)-5-Amino-6-cyclohexyl-4-hydroxy-2-isopropylhexanoyl N-[3-(Dimethylamino)propyl]amide (2S)-2-{(3R)-3-Benzyl-4-N-(4-methylpiperazin-1-yl-carbonyl)-2-keto-piperazin-1-yl }-hexanoic acid (300 mg, 0.7 mmol) was coupled with (2R,4S,5S)-5-amino-6-cyclohexyl-4-hydroxy-2-isopropylhexanoyl N-[3-(dimethylamino)-propyl]amide (250 mg) by the HOBT/NMM/EDAC procedure to afford crude product. Purification by flash chromatography on silic gel eluting with 10% methanol and 1% ammonium hydroxide in methylene chloride afforded the title product (106 mg, 20%). The 300 MHz $^1$H NMR spectrum was found to be consistent with the proposed structure. MS (FAB) m/e 768 (M+H)$^+$.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate. camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, phosphate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of formula (I) which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The prodrugs are metabolically converted in vivo to the parent compound of formula (I). The preparation of the prodrug esters is carried out by reacting a hydroxyl-substituted compound of formula (I) with an activated amino acyl, phosphoryl or hemisuccinyl derivative. The resulting product is then deprotected to provide the desired prodrug ester. Other prodrugs include a hydroxyl-substituted compound of formula (I) wherein the hydroxyl group is functionalized with a substituent of the formula —CH($R_{30}$)OC(O)$R_{31}$ or —CH($R_{30}$)OC(S)$R_{31}$ wherein $R_{31}$ is loweralkyl, haloalkyl, alkoxy, thioalkoxy or haloalkoxy and $R_{30}$ is hydrogen, loweralkyl, haloalkyl, alkoxycarbonyl, aminocarbonyl, alkylaminocarbonyl or dialkylaminocarbonyl. These prodrugs can be prepared by condensation of the hydroxyl group with an activated aldehyde followed by acylation of the intermediate hemiacetal.

The compounds of the present invention are useful for inhibiting Candida acid protease in mammals, especially humans. The compounds of the present invention are also useful for preventing or treating infections caused by Candida species in mammals, especially humans. The present invention also relates to the use of the compounds of the invention in combination with one or more other antifungal agents. Other antifungal agents are selected from the group consisting of amphotericin B, nystatin, flucytosine, ketoconazole, miconazole, clotrimazole, fluconazole and itraconazole.

The ability of the compounds of the invention to inhibit Candida acid protease can be demonstrated in vitro by the following method.

Isolation and Purification of *Candida albican* Acid Protease Organism and growth conditions. *Candida albicans* ATCC10231 was grown overnight in Sabouraud broth (Difco) at 30° C. Cells were centrifuged at 10,000xg for 10 min (4° C.) and the cell pellet washed once with 10 mM phosphate buffered saline (PBS), pH7.0. Washed cells ($6 \times 10^6$ colony forming units per mL) were grown in yeast nitrogen base without ammonium sulfate or amino acids (Difco), plus 2% glucose and 0.1% casein (nitrogen source) at 37° C.

Proteinase isolation. Maximum proteinase production was attained when the culture reached a pH of 3.5 to 4.0 (about 48 hrs). Cells were then harvested at 10,000xg for 20 min (4° C.) and the supernatant filtered through a 0.2μ acetate filter unit (Nalgen). The filtrate was concentrated on an Amicon concentrator (PM30 or YM10 membrane, 75 mm) and 30 mL of the concentrate was loaded onto a Cibacron blue F3GA-6% agarose (Pierce Chem.) column (1.5x44cm) equilibrated with 10 mM sodium citrate, pH 6.5, containing lmM EDTA and 0.02% sodium azide (Ray, T. L., and Payne, C. D. Infection and Immunity 58:508-514, 1990). Bovine serum albumin (BSA) was used as substrate to monitor the column for proteinase activity and to determine total proteolytic units. One BSA proteolytic unit was defined as an optical density (750 nm wavelength) increase of 0.100 under incubation conditions of 37° C. for 60 min (Remold, H., Fasold, H., and Staib, F. Biochimica et Biophysica Acta 167:399-406, 1968). Fractions with proteolytic activity were eluted in the void volume with equilibration buffer, pooled and stored at −70° C.

Proteinase purity and molecular weight was determined by the Phast-gel (12.5% acrylamide) electrophoresis system (Pharmacia). Protein was determined by the Lowry method (Lowry, O. H., Rosenbrough, N. J., Farr, A. L., and Randall, R. J. Journal of Biological Chemistry 193:263-275, 1951). A fluorogenic substrate, A78331, may also be used.to monitor proteinase production and purification. This substrate, DABCYL-Gaba-Ile-His-Pro-Phe-His-Leu-Val-Ile-His-Thr-EDANS (Holzman, T. F., Chung, C. C., Edalji, R., Egan, D. A., Gubbins, E. J., Rueter, A., Howard, G., Yang, L. K., Pederson, T. M., Krafft, G. A., and Wang, G. T. Journal of Protein Chemistry 9:663-672,. 1990) contains the fluorescent EDANS group, [5-(2-aminoethyl)-amino]naphthalene-1-sulfonic acid, which is quenched by the DABCYL group, 4-(4-dimethylaminophenylazo)benzoic acid, as long as it is part of the molecule (Matayoshi, E. D., Wang, G. T., Krafft, G. A., and Erickson, J. Science 247:954-958, 1990). Proteolysis of this compound by the fungal proteinase releases Thr-EDANS, which when activated at 340 nm fluoresces at 490 nm with the same intensity as equimolar EDANS. Activity is expressed in terms of nmol EDANS released from 32 μM A78331 under incubation conditions of 22° C. for 60 min. One BSA proteolytic unit was equivalent to 1.03 nmol EDANS released.

In Vitro Inhibitor Assay Method

Microtiter assay. The assay for inhibitors of *C. albicans* acid proteinase was done in microtiter trays with the fluorogenic substrate A78331. Test compounds were initially tested at 1μM, followed by a dose study ranging down to 0.2 nM for compounds having greater then 80% inhibition from control at the 1 μM dose. The reaction mixture consisted of 5μL test compound or dimethyl sulfoxide and 45μL of fungal proteinase (0.13 BSA proteolytic units or 0.13 nmol EDANS released) in 50 mM sodium citrate, pH 4.5, which was preincubated at 22° C. for 30 min. The reaction was started with the addition of 50μL fluorogenic substrate in citrate buffer and the incubation was continued at 22° C. for 90 min. The reaction was terminated with 150μL pepstatin (final concentration of 1μM) and 210μL samples were transfered to microfluor plates for fluorescence quantitation in a luminescence spectrophotometer (Perkin-Elmer model LS-50). The excitation wavelength was 340 nm and the emission was monitored at 490 nm (430 nm filter employed). Inhibition was expressed as % change in relative intensity from the dimethyl sulfoxide control group (no inhibitor). $IC_{50}$'s were determined from plots of log dose versus % inhibition from control.

When tested in accordance with the foregoing procedure, the compounds of the invention were found to inhibit *Candida alicans* acid protease with $IC_{50}$'s as shown in Table I.

TABLE I

| Example | $IC_{50}$ (nM) |
|---|---|
| 1 | 1.3 |
| 3 | 30.1 |
| 5 | 13.3 |
| 11 | 85 |
| 12 | 3.8 |
| 13 | 2.7 |
| 14 | 4.5 |
| 15 | 3.8 |
| 16 | 5.0 |
| 17 | 6.2 |

TABLE I-continued

| Example | IC$_{50}$ (nM) |
|---------|----------------|
| 18 | 3.8 |

The data demonstrates that the compounds of the invention are inhibitors of *Candida albicans* acid protease.

The ability of a compound of the invention to treat an infection caused by a CandIda species can be demonstrated in vitro according to the methods outlined by El-Maghrabi, et al., Clin. Exp. Dermatol. 15 183 (1990); Ghannoum,, J. Appl. Bacteriol. 68 163 (1990); and Ray, et al., J. Invest. Dermatol. 83 37 (1984).

The ability of a compound of the invention to treat an infection caused by a Candida species can be demonstrated in vivo according to the methods outlined by Ray, et al., J. Invest. Dermatol. 66 29 (1976); Ray, et al., Infect. Immun. 56 1942 (1988); Van Cutsem,, et al., Sabouraudia 9 17 (1971); Sohnie, et al., J. Immunol. 117 523 (1976); Kobayashi, et al., Microb. Immunol. 33 709 (1989); Shimizu, et al., Microb. Immunol. 31 1045 (1987); Zotter, et al., Dermatol. Mon. Schr. 176 189 (1990); and Ruchel, et al., Zbl. Bakt. 273 391 (1990).

The ability of a compound of the invention to prevent an infection caused by a Candida species can be demonstrated according to the methods outlined by Meitner, et al., Infect. Immun. 58 2228 (1990) and Cole, et al., Mycoses 33 7 (1990).

Total daily dose of a compound of the invention administered to a human or other mammal in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spfay, rectally, or topically in dosage unit formulations containing conventional nontoxic pharmaceutically acceptable carriers, adjuvants, and vehicles as desired. Topical dosages can be in the form of salves, powders, sprays, ointments, lotions, creams, solutions, suspensions and the like. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal or vaginal administration of the drug can be prepared by mixing the drug with a suitable nonirritating excipient such as cocoa butter and polyethylene glycols which are solid at ordinary temperatures but liquid at the rectal or vaginal temperature and will therefore melt in the rectum or vagina and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

When the compound of the invention is administered in combination with another antifungal agent, the compound of the invention and the other antifungal agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for inhibiting Candida acid protease comprising administering to a mammal in need of such treatment a therapeutically effective amount of a compound of the formula:

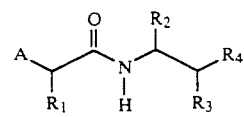

wherein $R_1$ is loweralkyl, loweralkenyl, cycloalkyl, cycloalkenyl, cycloalkylalkyl, cycloalkenVlalkyl. arylalkyl or (heterocyclic)alkyl;

$R_2$ is loweralkyl, cycloalkylalkyl or arylalkyl;

$R_3$ is —OH or —NH$_2$;

$R_4$ is (a) —CH(OH)—R₅ wherein R₅ is loweralkyl, cycloalkyl or cycloalkylalkyl or (b) —CH₂CH(R₆)C(O)NHR₇ wherein R₆ is loweralkyl and R7 is loweralkyl, aminoalkyl, alkylaminoalkyl, dialkylaminoalkyl, hydroxyalkyl, alkoxyalkyl, thioalkoxyalky, carboxyalkyl, alkoxycarbonylalkyl, cyanoalkyl or (heterocyclic)alkyl; and

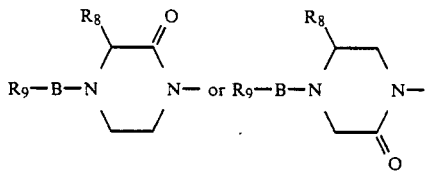
(a)

wherein R₈ is arylalkyl, B is —C(O) or —S(O)₂— and R₉ is aryl, arylakly, heterocyclic or (heterocyclic)alkyl; or

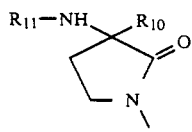
(b)

wherein R₁₀ is arylalkyl and R₁₁ is (a) —C(O)R₁₂ wherein R₁₂ is alkoxy, arylalkoxy, aryl, arylalkyl, heterocyclic or (heterocyclic)alkyl or (b) —S(O)-2—R₁₃ is aryl, arylalkyl, heterocyclic or (heterocyclic)alkyl; or a pharmaceutically acceptable salt, ester or prodrug thereof.

2. The method of claim 1, wherein the Candida acid protease is *Candida albicans* protease.

3. The method of claim 1 wherein A is

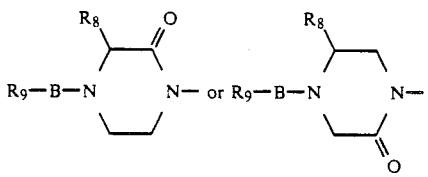

wherein R₈ is arylalkyl, B is —C(O) or —S(O)₂— and R₉ is aryl, arylalkyl, heterocyclic or (heterocyclic)alkyl; R₁ is loweralkyl; R₂ is cycloalkylalkyl and R₄ is —CH₂CH(R₆)C(O)NHR₇ wherein R₆ is loweralkyl and R7 is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl.

4. A method for inhibiting Candlda acid protease comprising administering to a mammal in need of such treatment a therapeutically effective amount of a compound of the formula

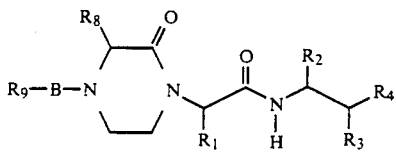

wherein R₁ is loweralkyl, loweralkenyl, cycloalkyl, cycloalkenyl, cycloalkylalkyl or cycloalkenylalkyl;

R₂ is loweralkyl, cycloalkylalkyl or arylalkyl;
R₃ is —OH or —NH₂;
R₄ is —CH₂CH(R₆)C(O)NHR₇ wherein R₆ is loweralkyl and R₇ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl; R₈ is arylalkyl;
R₈ is arylalkyl;
B is —C(O) or —S(O)₂—; and
R₉ is aryl, arylalkyl, heterocyclic or (heterocyclic)alkyl; or a pharmaceutically acceptable salt, ester or prodrug thereof.

5. The method of claim 4 wherein the Candida acid protease is *Candida albicans* acid protease.

6. A method for inhibiting Candida acid protease comprising administering to a mammal in need of such treatment a therapeutically effective amount of a compound of the formula:

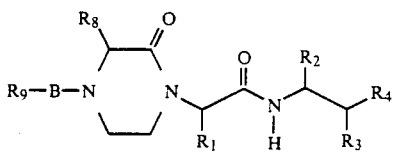

wherein R₁ is loweralkyl;
R₂ is cycloalkylalkyl;
R₃ is —OH;
R₄ is —CH₂CH(R₆)C(O)NHR₇ wherein R₆ is loweralkyl and R₇ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl;
R₈ is arylalkyl;
B is —C(O) or —S(O)₂—; and
R₉ is aryl, arylalkyl, heterocyclic or (heterocyclic)alkyl; or a pharmaceutically acceptable salt, ester or prodrug thereof.

7. The method of claim 6 wherein the Candida acid protease is *Candida albicans* acid protease.

8. The method of claim 6 wherein R₂ is cyclohexylmethyl and R₈ is benzyl.

9. A method for preventing or treating a Candida species fungal infection comprising administering to a mammal in need of such treatment a therapeutically effective amount of a compound of the formula:

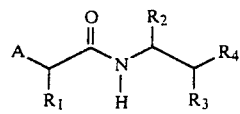

wherein R₁ is loweralkyl, loweralkenyl, cycloalkyl, cycloalkenyl, cycloalkylalkyl, cycloalkenylalkyl, arylalkyl or (heterocyclic)alkyl;
R₂ is loweralkyl, cycloalkylalkyl or arylalkyl;
R₃ is —OH or —NH₂;
R₄ is
(a) —CH(OH)-R₅ wherein R⁵ is loweralkyl, cycloalkyl or cycloalkylalkyl or
(b) —CH₂CH(R₆)C(O)NHR₇ wherein R₆ is loweralkyl and R₇ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl; and A is

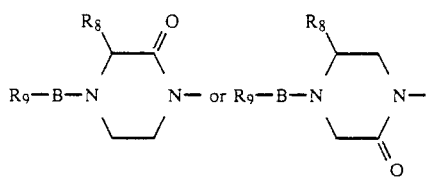

wherein $R_8$ is arylalkyl, B is —C(O) or —S(O)$_2$— is aryl, arylalkyl, heterocyclic or (heterocyclic)alkyl; or

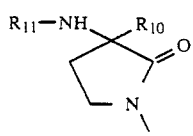

wherein $R_{10}$ is arylalkyl and $R_{11}$ is (a) —C(O)$R_{12}$ wherein $R_{12}$ is alkoxy, arylalkoxy, aryl, arylalkyl, heterocyclic or (heterocyclic)alkyl or (b) —S(O)$_2$—$R_{13}$ wherein $R_{13}$ is aryl, arylalkyl, heterocyclic or (heterocyclic)alkyl; or a pharmaceutically acceptable salt, ester or prodrug thereof.

10. The method of claim 9 wherein the Candida species is *Candida albicans*.

11. The method of claim 9 wherein A is

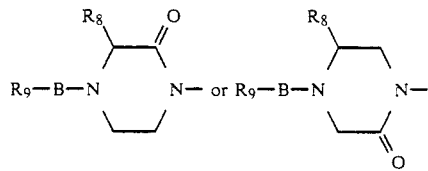

wherein $R_8$ is arylalkyl, B is —C(O) or —S(O)$_2$— and $R_9$ is aryl, arylalkyl, heterocyclic or (heterocyclic) alkyl; $R_1$ is loweralkyl; $R_2$ is cycloalkylalkyl and $R_4$ is —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl.

12. The method of claim 9 further comprising administering a therapeutically effective amount of an additional antifungal agent useful for treating fungal infections caused by Candida species.

13. A method for preventing or treating a Candida species fungal infection comprising administering to a mammal in need of such treatment a therapeutically effective amount of a compound of the formula:

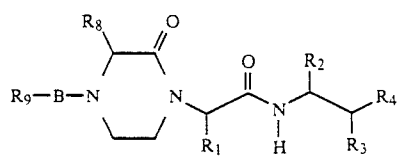

wherein $R_1$ is loweralkyl, loweralkenyl, cycloalkyl, cycloalkenyl, cycloalkylalkyl or cycloalkenylalkyl;
$R_2$ is loweralkyl, cycloalkylalkyl or arylalkyl;
$R_3$ is —OH or —NH$_2$;
$R_4$ is —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl;
$R_8$ is arylalkyl;
B is —C(O) or —S(O)$_2$—; and
$R_9$ is aryl, arylalkyl, heterocyclic or (heterocyclic)alkyl; or a pharmaceutically acceptable salt, ester or prodrug thereof.

14. The method of claim 13 wherein the Candida species is *Candida albicans*.

15. A method for preventing or treating a Candida species fungal infection comprising administering to a mammal in need of such treatment a therapeutically effective amount of a compound of the formula:

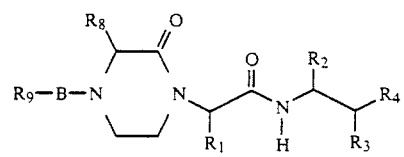

wherein $R_1$ is loweralkyl;
$R_2$ is cycloalkylalkyl;
$R_3$ is —OH;
$R_4$ is —CH$_2$CH($R_6$)C(O)NHR$_7$ wherein $R_6$ is loweralkyl and $R_7$ is loweralkyl, aminoalkyl, alkylaminoalkyl, dialkylaminoalkyl, hydroxyalkyl, alkoxyalkyl, thioalkoxyalkyl, carboxyalkyl, alkoxycarbonylalkyl, cyanoalkyl or (heterocyclic)alkyl;
$R_8$ is arylalkyl;
B is —C(O) or —S(O)$_2$—; and
$R_9$ is aryl, arylalkyl, heterocyclic or (heterocyclic)alkyl; or a pharmaceutically acceptable salt, ester or prodrug thereof.

16. The method of claim 15 wherein the Candida species is *Candida albicans*.

17. The method of claim 15 wherein $R_2$ is cyclohexylmethyl and $R_8$ benzyl.

* * * * *